(12) United States Patent
Ho et al.

(10) Patent No.: US 9,138,594 B2
(45) Date of Patent: Sep. 22, 2015

(54) LIGHT EMITTING DIODE-BASED SKIN COSMETIC DEVICE

(71) Applicant: GCSOL Tech Co., Ltd., Taichung County (TW)

(72) Inventors: Fang-Chuan Ho, Hsinchu (TW); Jui-Fen Pai, Nantou County (TW); Tien-Jung Huang, Taipei (TW); Chin-Chao Lee, New Taipei (TW)

(73) Assignee: GCSOL Tech Co., Ltd., Taichung (TW)

( * ) Notice: Subject to any disclaimer, the term of this patent is extended or adjusted under 35 U.S.C. 154(b) by 125 days.

(21) Appl. No.: 13/854,127

(22) Filed: Mar. 31, 2013

(65) Prior Publication Data
US 2014/0222118 A1    Aug. 7, 2014

(30) Foreign Application Priority Data
Feb. 5, 2013 (TW) .............................. 102104422 A

(51) Int. Cl.
*A61N 5/06* (2006.01)
(52) U.S. Cl.
CPC ....... *A61N 5/0616* (2013.01); *A61N 2005/0651* (2013.01)

(58) Field of Classification Search
CPC .................. A61N 5/0616; A61N 2005/0651; F21V 15/01
See application file for complete search history.

(56) References Cited

U.S. PATENT DOCUMENTS

| 5,259,380 A | 11/1993 | Mendes et al. | |
|---|---|---|---|
| 2006/0020309 A1* | 1/2006 | Altshuler et al. | 607/88 |
| 2006/0229689 A1* | 10/2006 | Ferguson et al. | 607/88 |
| 2007/0027440 A1* | 2/2007 | Altshuler et al. | 606/9 |
| 2012/0104277 A1 | 5/2012 | Morren | |

* cited by examiner

*Primary Examiner* — Gary Jackson
*Assistant Examiner* — Scott T Luan
(74) *Attorney, Agent, or Firm* — CKC & Partners Co., Ltd.

(57) ABSTRACT

A light emitting diode-based skin cosmetic device includes a first light emitting panel, a second light emitting panel, a first narrow band filter, a second narrow band filter and an optical window. The first light emitting panel is connected with the second light emitting panel at one side and an angle is formed between the first light emitting panel and the second light emitting panel. Two sides of the optical windows are connected with the first light emitting panel and the second light emitting panel together to form a triangle structure and the angle is faced toward the optical windows. The first and second narrow band filter is disposed on one surface of the first light to emitting panel and one surface of the second light emitting panel respectively.

11 Claims, 9 Drawing Sheets

LIGHT EMITTING DIODE-BASED SKIN COSMETIC DEVICE

RELATED APPLICATIONS

The application claims priority to Taiwan Application Serial Number 102104422, filed on Feb. 5, 2013, which is herein incorporated by reference.

BACKGROUND

1. Technical Field

The present invention relates to a light-based skin cosmetic device, especially relates to a light emitting diode-based skin cosmetic device which utilizes multiple organic light emitting diode panels as lighting source.

2. Description of Related Art

An appearance of an individual is taking more weight in the modernization of the society. Skin is covering the human body not only protecting the body, but also determining the first impression of other people. Therefore, new cosmetic or therapy methods in need have constantly been developed. Conventional therapy method is directed to smearing a cosmetic or a medicine on the skin directly. Owing to the direct contact of the chemical component of the cosmetic or medicine with the skin, a variety of side effects such as skin allergy, skin dermatitis, or skin diseases may possibly occur. Therefore, demanding on new cosmetic or therapy methods are increasing.

Phototherapy is a newly developed technology on skin care and therapy. The phototherapy normally includes process of irradiating a light to the skin first, and makes the energy of light be transferred into thermal or chemical energy after the light is absorbed by the skin, so as to lead to series reactions in the skin and to increase the hyperplasia and activation of the cell. Laser light and pulse light are commonly used as the light sources in the phototherapy process. Several wavelength bands can be used for different therapy purpose. For example, red light with 633 nm to 650 nm wavelength band penetrates up to 8-10 mm beneath the skin, inhibiting the inflammatory process and stimulating the re-growth of the skin cell; blue light with 415 nm to 462 nm wavelength band penetrates up to 0.5 mm beneath the skin, regulating skin sebum secretion and anti-bacterial properties; green light with 527 nm is for skin comforting and rejuvenation. Besides, yellow light with 590 nm is able to stimulate fibroblasts, and orange light with 525 nm to decompose pigment of the skin and produce a lighter skin color.

Among the phototherapy processes, the laser light source may easily cause hazards on the skin surface due to intense energy thereof and careless operations. Further, the laser light cannot destroy the artery in the deeper level; this will cause the black pigment re-condensing and the dark spot regaining. The pulse light utilizes ionized gas as light source, such that the wavelength band and intensity of the pulse light are limited to the selection of parameters like the species of the gas, the quantity of the gas, and the control voltage. Another phototherapy process utilizes light emitting diode matrix as light source, which the light emitting diode matrix is composed of inorganic light emitting diode units; this will leads to the un-controlled heat dissipation, and the light uniformity. Phototherapy may eliminate side effects of the conventional skin therapy, but the complicated operation procedure and the large equipment still lead to high cost and difficult operation for those who have needs of safe and convenient make-up or therapy at home.

SUMMARY

According to one aspect of the present disclosure, a light emitting diode-based skin cosmetic device is provided. The light emitting diode-based skin cosmetic device includes a first light emitting diode panel, a first narrow band filter, a second light emitting diode panel, a second narrow band filter and an optical window. The first narrow band filter is disposed on one surface of the first light emitting diode panel, and the second narrow band filter is disposed on one surface of the second light emitting diode panel. The second light emitting diode panel is connected with one side of the first light emitting diode panel, and an angle is formed between the first light emitting to diode panel and the second light emitting diode panel. Two sides of the optical window are connected with the other side of the first light emitting diode panel and the other side of the second light emitting diode panel respectively to form a triangle structure, and the angle between the first light emitting diode panel and the second light emitting diode panel is faced toward the optical window. Wherein, the first light emitting diode panel emits a first wavelength band through the first narrow band filter, the second light emitting diode panel emits a second wavelength band through the second narrow band filter, and the first wavelength band and the second wavelength band are irradiated into a human's skin through the optical window.

According to another aspect of the present disclosure, a light emitting diode-based skin cosmetic device is provided. The light emitting diode-based skin cosmetic device includes a first light emitting diode panel, a second light emitting diode panel, an optical window and a narrow band filter. The second light emitting diode panel is connected with one side of the first light emitting diode panel, and an angle is formed between the first light emitting diode panel and the second light emitting diode panel. Two sides of the optical window are connected with the other side of the first light emitting diode panel and the other side of the second light emitting diode panel respectively to form a triangle structure, and the angle between the first light emitting diode panel and the second light emitting diode panel is faced toward the optical window. The narrow band filter is disposed on a surface of the optical window. Wherein the first light emitting diode panel emits a first wavelength band, the second light emitting diode panel emits a second wavelength band, and the first wavelength band and the second wavelength band are irradiated to a human's skin through the optical window.

According to still another aspect of the present disclosure, a light emitting diode-based skin cosmetic device is provided. The light emitting diode-based skin cosmetic device includes a plurality of double-faced light emitting panels and a plurality of optical windows. Each of the double-faced light emitting panels comprises at least one light emitting diode source to form a flat type lighting, wherein the plurality of double-faced light emitting panels are connected with each other at one side, and an angle is formed between each two adjacent double-faced light emitting panels. Two sides of each optical window are connected with open side of the two adjacent double-faced light emitting panels to form a triangle structure, and the angle between each two adjacent double-faced light emitting panels is faced toward each of the optical window.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
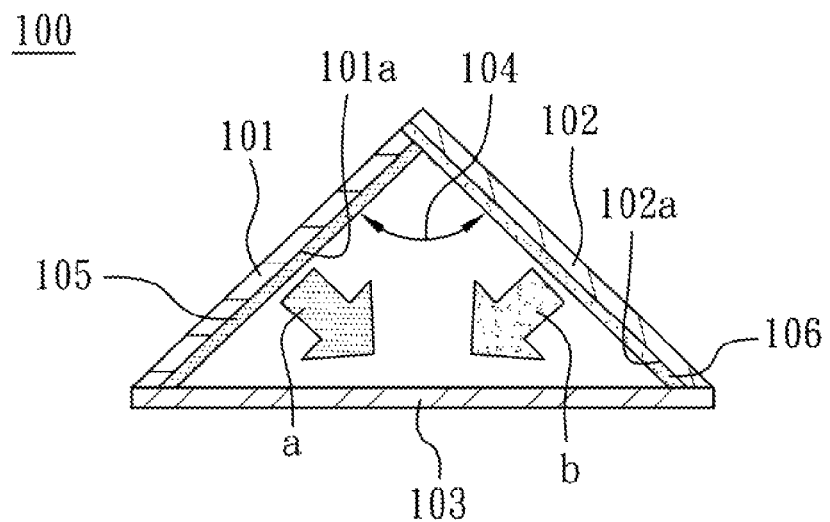
FIG. 1 is a side view of a light emitting diode-based skin cosmetic device according to one embodiment of the present disclosure.

FIG. 1 is a side view of a light emitting diode-based skin cosmetic device 100 according to one embodiment of the present disclosure. The light emitting diode-based skin cosmetic device 100 includes, a first light emitting diode panel 101, a second light emitting diode panel 102, an optical window 103, a first narrow band filter 105, and a second narrow band filter 106. One side of the first light emitting diode panel 101 is connected with the second light emitting diode panel 102, and an angle 104 is formed between the first light emitting diode panel 101 and the second light emitting diode panel 102. One side of the optical window 103 is connected with the first light emitting diode panel 101, and the other side of the optical window 103 is connected with the second light emitting diode panel 102. The angle 104 is faced toward the optical window 103 and the first light emitting diode panel 101, the second light emitting diode panel 102, and the optical window 103 are connected together to form a triangle structure. The first narrow band filter 105 is disposed on a surface 101a of the first light emitting diode panel 101, and the second narrow band filter 106 is disposed on a surface 102a of the second light emitting diode panel 102. The first light emitting diode panel 101 emits a first wavelength band a through the first narrow band filter 105, and the second light emitting diode panel 102 emits a second wavelength band b through the second narrow band filter 106. The first wavelength band a and the second wavelength band b are irradiated to human's skin through the optical window 103, and a thermal energy and chemical energy is produced after the light being absorbed by the skin, and therefore achieving cell activation effect. The first light emitting diode panel 101 and the second light emitting diode panel 102 can utilize organic light emitting diode panels as lighting source; therefore a uniform light shape is obtained. The first wavelength band a and the second wavelength band b can be the same or different. When the first wavelength band a and the second wavelength band b are the same, the wavelength can be selected from one of 450±10 nm, 595±10 nm, 525±10 nm or 640±10 nm, and a uniform light can be obtain through the optical windows 103. When the first wavelength band a and the second wavelength band b are different, the wavelength can be selected from any two of 450±10 nm, 595±10 nm, 525±10 nm or 640±10 nm; therefore multiple therapy effects are obtained. Moreover, the first wavelength band a and the second wavelength band b can be overlapped on the optical window 103, and a third wavelength band is obtained according to the color chromatic principle, therefore the application range can be extended. When apply the first and second narrow band filter (105, 106) to the first and second light emitting diode panel (101, 102), a precision controllability on the wavelength band is obtained, and a more uniform light intensity is irradiated to skin for achieving better therapy or cosmetic effect.

Figure 2:
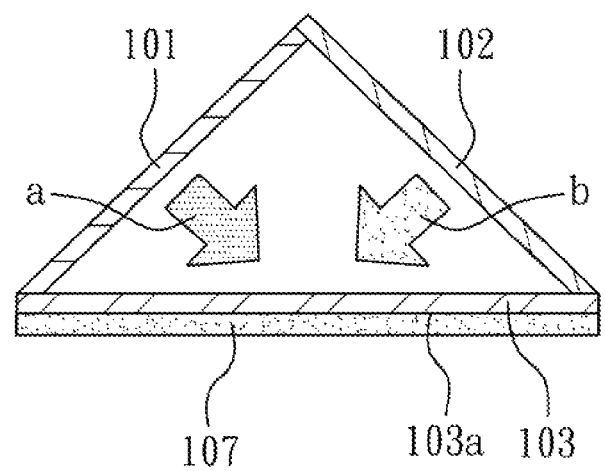
FIG. 2 is a side view showing another embodiment of the narrow band filter in FIG. 1.

FIG. 2 is a side view showing another embodiment of the first and the second narrow band filter (105, 106) in FIG. 1. In FIG. 1, the first narrow band filter 105 and the second narrow band filer 106 each is a single frequency-range narrow band filter in that the light emitted from the first light emitting diode panel 101 and the second light emitting diode panel 102 are all single narrow wavelength bands of a few nm's wide. In FIG. 2, a narrow band filter 107 with multiple frequency-ranges is used. The narrow band filter 107 is disposed on a surface 103a of the optical window 103. Therefore, the first light emitting diode panel 101 and the second light emitting diode panel 102 can be combined together to emit lights with multiple bands through the multiple frequency-range narrow band filter 107. Thus, only a narrow band filter 107 is needed for transmitting multiple frequencies instead of using two narrow band filters (105, 106); therefore a simpler structure of the light emitting diode-based skin cosmetic device 100 is obtained for reducing the manufacturing cost.

Figure 3:
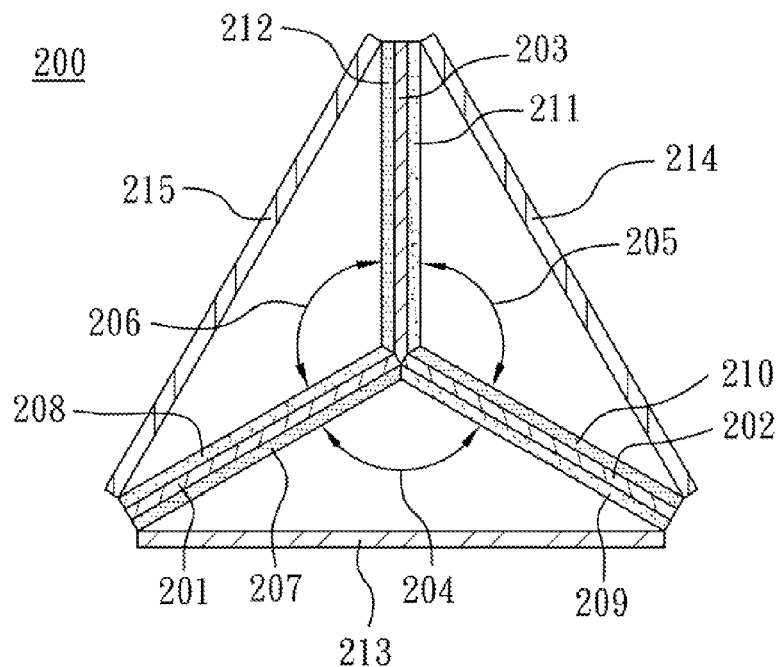
FIG. 3 is a side view of a light emitting diode-based skin cosmetic device according to another embodiment of the present disclosure.

FIG. 3 is a structural side view of a light emitting diode-based skin cosmetic device 200 according to another embodiment of the present disclosure. The light emitting diode-based skin cosmetic device 200 includes three double-faced light emitting panels 201, 202, and 203; six narrow band filters 207, 208, 209, 210, 211 and 212; and three optical windows 213, 214 and 215. Double-faced light emitting panels 201, 202, and 203 utilize organic light emitting panel as lighting source. One side of each of the double-faced light-emitting panel 201, 202, and 203 is interconnected with each other to form a radiation-liked appearance. An angle 204 is formed between the double-faced light emitting panel 201 and 202, an angle 205 is formed between the double-faced light emitting panel 202 and 203, and an angle 206 is formed between the double-faced light emitting panel 203 and 201. Two sides of the optical window 213 are connected with an open side of the double-faced light-emitting panel 201 and the double-faced light-emitting panel 202 respectively to form a triangle structure. Similarly, the double-faced light emitting panel 202, the double-faced light emitting panel 203, and the optical window 214 are connected to form a triangle structure; and the double-faced light emitting panel 203, the double-faced light emitting panel 201, and the optical window 215 are connected to form a triangle structure. The double-faced light emitting panels 201 and 202 emit lights through the optical window 213, the double-faced light emitting panels 202 and 203 emit lights through the optical window 214, and the double-faced light emitting panels 203 and 201 emit lights through the optical window 215. The double-faced light-emitting panel 201 can emit the same or different wavelength band of light in the two sides, the same as the double-faced light-emitting panel 202 and 203.

Figure 4:
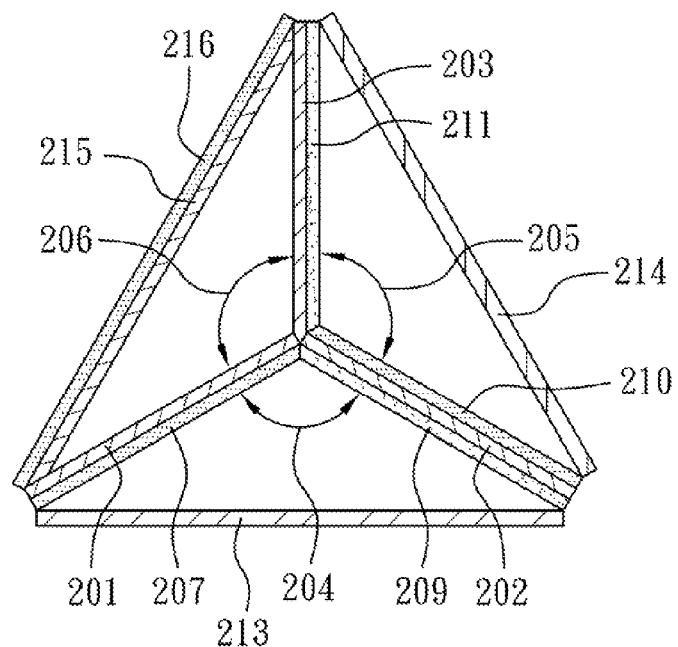
FIG. 4 is a side view of another embodiment of the light emitting diode-based skin cosmetic device in FIG. 3.

FIG. 4 is a side view of another embodiment of the light emitting diode-based skin cosmetic device 200 in FIG. 3. In FIG. 3, each light emitted from the two different sides of the double-faced light emitting panels 201, 202 and 203 is a single frequency-range light, thus a narrow band filter is necessary to be disposed on each side of the double-faced light-emitting panels 201, 202 and 203. In FIG. 4, the light emitting diode-based skin cosmetic device 200 without using the narrow band filter 208 disposed on one side of the double-faced light emitting panel 201 and the narrow band filter 212 disposed on one side of the double-faced light emitting panel 203, but a narrow band filter 216 with multiple frequency-range disposed on one side of the optical window 215.

Figure 5:
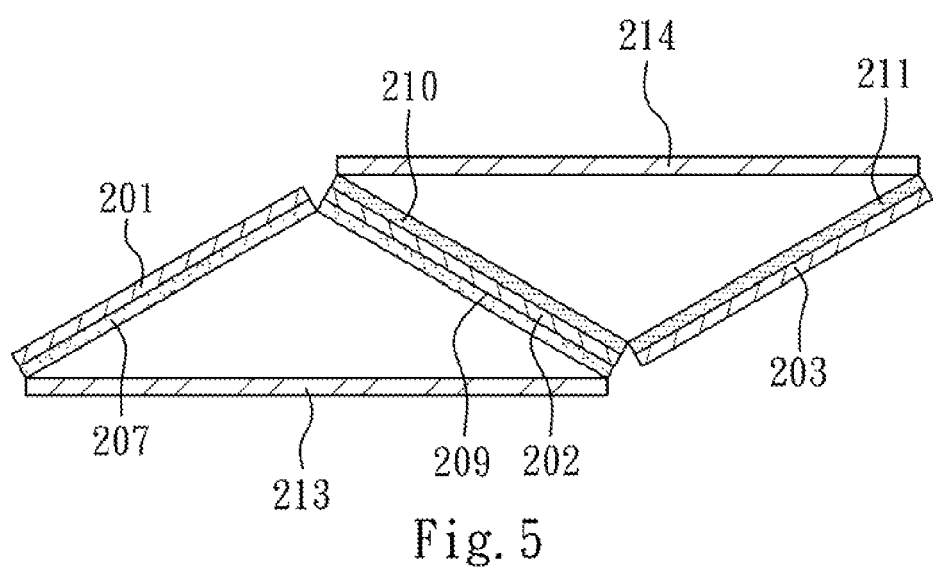
FIG. 5 is a side view of still another embodiment of the light emitting to diode-based skin cosmetic device in FIG. 3.

FIG. 5 is a side view of still another embodiment of the light emitting diode-based skin cosmetic device 200 in FIG. 3. In FIG. 3, one side of each of the double-faced light emitting panels 201, 202, and 203 is interconnected with each other to form a radiation-liked appearance. In FIG. 5, one side of each of the double-faced light emitting panels 201, 202, and 203 is interconnected with each other to form a serration-liked appearance. Similarly, the narrow band filter 207, 209 are disposed on one side of the double-faced light emitting panel 201, 202, and the narrow band filters 210, 211 are disposed on the other side of the double-faced light emitting panel 202 and one side of the double-faced light emitting panel 203 respectively. Two sides of the optical window 213 are connected with the open side of the double-faced light emitting panel 201 and the double-faced light emitting panel 202 to form a triangle structure; and two sides of the optical window 214 are connected with the open side of the double-faced light emitting panel 202 and the double-faced light emitting panel 203 to form a triangle structure. Therefore, the double-faced light emitting panels 201, 202 emit lights through the optical window 213, and the double-faced light emitting panels 202, 203 emit lights through the optical window 214.

Figure 6A:
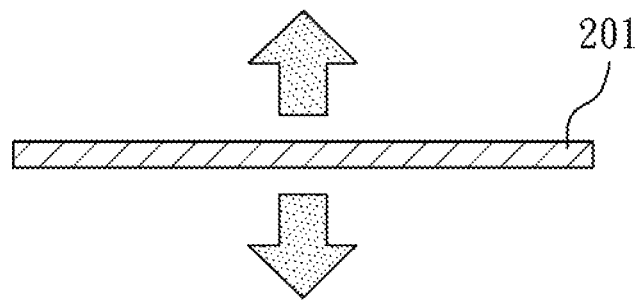
FIGS. 6A and 6B are schematic views of two embodiments of the double-faced light emitting panel.
Figure 6B:
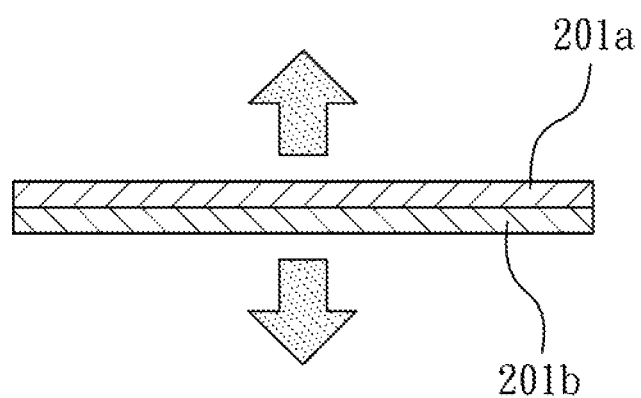

FIGS. 6A and 6B are schematic views of two embodiments of the double-faced light emitting panel 201. For achieving double-faced lighting, In FIG. 6A, a double-faced light emitting panel 201 utilizes a double-faced lighting organic light emitting diode panel as lighting source. In FIG. 6B, two organic light emitting diode panels 201a, 201b, each with single-faced lighting are used to composite the double-faced light emitting panel 201.

Figure 7:
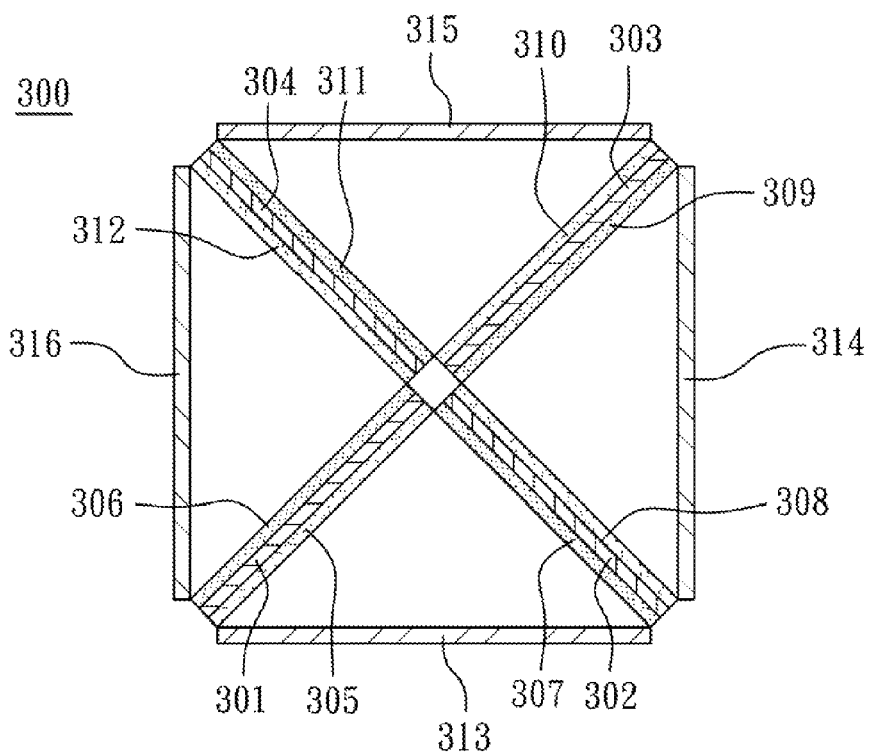
FIG. 7 is a side view of a light emitting diode-based skin cosmetic device according to still another embodiment of the present disclosure.

FIG. 7 is a structural side view of a light emitting diode-based skin cosmetic device 300 according to still another embodiment of the present disclosure. The light emitting diode-based skin cosmetic device 300 includes four double-faced light emitting panels 301, 302, 303 and 304; eight narrow band filters 305, 306, 307, 308, 309, 310, 311 and 312; and four optical windows 313, 314, 315 and 316. Double-faced light emitting panels 301, 302, 303 and 304 utilize organic light emitting diode panel as lighting source. One side of each of the double-faced light emitting panels 301, 302, 303 and 304 is interconnected with each other to form a radiation-liked appearance. Two sides of the optical window 313 are connected with an open side of the double-faced light-emitting panel 301 and the double-faced light emitting panel 302 respectively to form a triangle structure.

Similarly, the double-faced light emitting panel 302, the double-faced light emitting panel 303, and the optical window 314 are connected to form a triangle structure; the double-faced light emitting panel 303, the double-faced light emitting panel 304, and the optical window 315 are connected to form a triangle structure; and the double-faced light emitting panel 304, the double-faced light emitting panel 301, and the optical window 316 are connected to form a triangle structure. The double-faced light emitting panels 301 and 302 emit lights through the optical window 313; the double-faced light emitting panels 302 and 303 emit lights through the optical window 314; the double-faced light emitting panels 303 and 304 emit lights through the optical window 315; and the double-faced light emitting panels 304 and 301 emit lights through the optical window 316. The double-faced light emitting panel 301 can emit the same or different wavelength band in two sides, the same as the double-faced light emitting panels 302, 303 and 304. The narrow band filter 305 and the narrow band filter 306 are disposed on two surfaces of the double-faced light emitting panel 301; the narrow band filter 307 and the narrow band filter 308 are disposed on two surfaces of the double-faced light emitting panel 302; the narrow band filter 309 and the narrow band filter 310 are disposed on two surfaces of the double-faced light emitting panel 303; and the narrow band filter 311 and the narrow band filter 312 are disposed on two surfaces of the double-faced light emitting panel 304. Therefore, the light emitting diode-based skin cosmetic device 300 can have eight different wavelength bands, thus a wider therapy range is obtained.

From several embodiments descried above, it is known that the light emitting diode-based skin cosmetic device of the disclosure is an extension of the based triangle structure which is formed by the interconnection of the first light emitting diode panel 101, the second light emitting diode panel 102, and the optical window 103 in FIG. 1. The basic triangle structure can have various assembling type to be applied in different conditions. Therefore, the various light emitting diode-based skin cosmetic devices of the disclosure can have multiple wavelength bands for achieving different therapy or cosmetic effect without extending the volume thereof.

Meanwhile, the light emitting diode-based skin cosmetic device of the disclosure utilizes organic light emitting diode panels and narrow band filters for achieving better controllability on the emitting light. The following embodiments are several examples of co-usages of the organic light emitting diode panels and the narrow band filters. The structure of the light emitting diode-based skin cosmetic device of the following embodiments is the same as FIG. 1. The first light emitting diode panel 101 and the second light emitting diode panel 102 utilize organic light emitting diode panels as lighting source, and the emitting wavelength bands of the first light emitting diode panel 101 and the second light emitting diode panel 102 are chosen as peaked at wavelengths 525±10 nm and 595±10 nm respectively for demonstration in the following embodiments.

Figure 8:
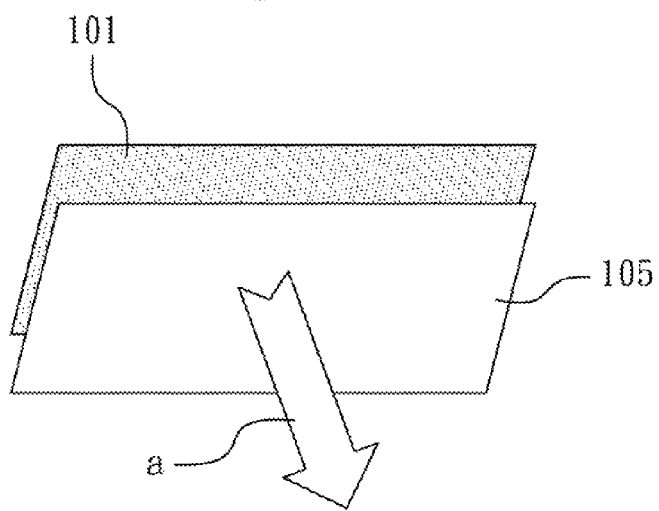
FIG. 8 is a schematic view showing a combination of the first light emitting diode panel and the narrow band filter of FIG. 1.

FIG. 8 is a schematic view showing a combination of the first light emitting diode panel 101 and the narrow band filter 105 of FIG. 1. When the first light emitting diode panel 101 utilizes an organic light emitting diode panel as lighting source, a FWHM of the lighting spectrum is wider and the peak wavelength is hard to be precisely controlled. Through the narrow band filter 105, a narrower FWHM (Full Width Half Maximum) of the spectrum and a precision control of the peak wavelength are obtained.

Figure 9:
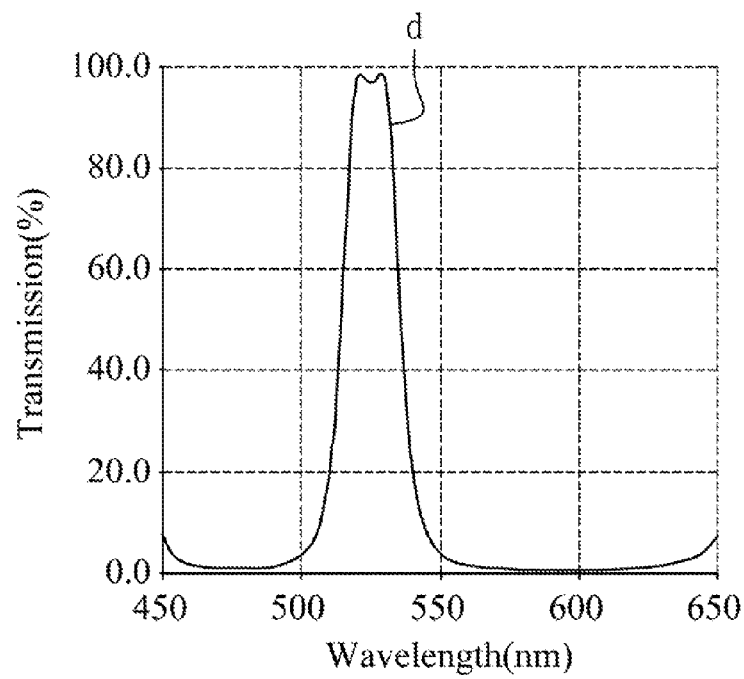
FIG. 9 is a transmission spectrum of the first narrow band filter.

FIG. 9 is a transmission spectrum of the first narrow band filter 105. In one embodiment, a transmission spectrum d of the first narrow band filter 105 shows a peak wavelength at 525 nm. The first narrow band filter 105 is made by vacuum coating method. The first narrow band filter 105 is made of a stacked structure on a substrate, in which the stacked structure includes 19 layers of overlapping of high/low refractive index layers. The thickness of the stacked structure is 1.52 μm. When a light source pass through the first narrow band filter 105, the FWHM of the spectrum is 20 nm.

Figure 10:
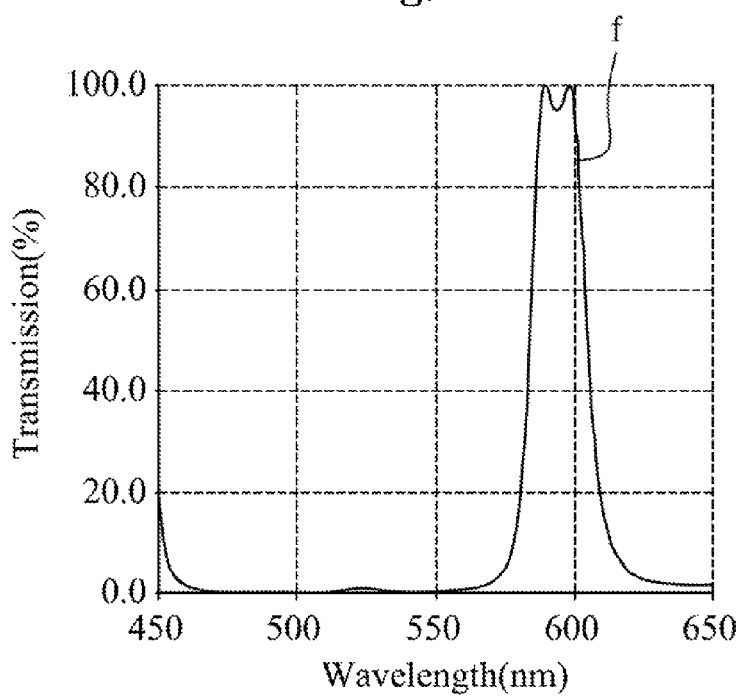
FIG. 10 is a transmission spectrum of the second narrow band filter.

FIG. 10 is a transmission spectrum of the second narrow band filter 106. In one embodiment, a transmission spectrum f of the second narrow band filter 106 shows a peak wavelength at 595 nm. The second narrow band filter 106 is made by vacuum coating method. The second narrow band filter 106 is made of a stacked structure on a substrate, in which the stacked structure includes 23 layers of overlapping of high/low refractive index layers. The thickness of the stacked structure is 2.03 μm. When light source passes through the second narrow band filter 106, the FWHM of the spectrum is 20 nm.

Figure 11:
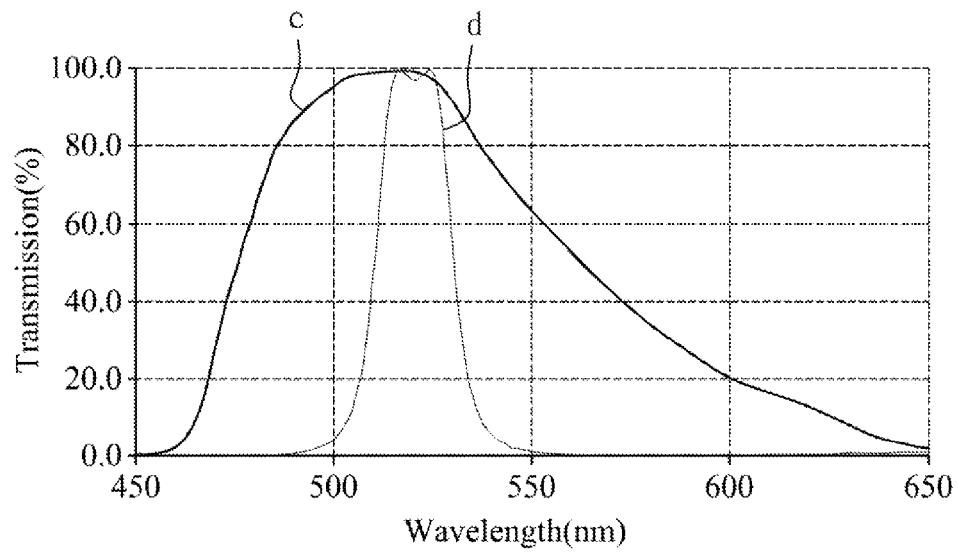
FIG. 11 is a combined-spectrum of a combination of the first light emitting diode panel and the first narrow band filter.

FIG. 11 is a combined-spectrum of a combination of the first light emitting diode panel 101 and the first narrow band filter 105. When the first light emitting diode panel 101 utilizes organic light emitting diode panel as lighting source, the FWHM of the spectrum c of the first light emitting diode panel 101 is wider, and the peak wavelength is hard to be precisely controlled although it is pre-determined as 525 nm. Through the first narrow band filter 105, a narrower FWHM of the spectrum and a precision control of the peak wavelength are obtained. Owing to the effect of the first narrow band filter 105, only wavelength band that matches with the wavelength bands of the spectrum d can pass through the first narrow band filter 105. Therefore, through the first narrow band filter 105, the emitting light can be concentrated and the uniformity of the light intensity can be enhanced. In addition, unnecessary wavelength band can be filtered for reducing the bad influence on the therapy of cosmetic effect.

Figure 12:
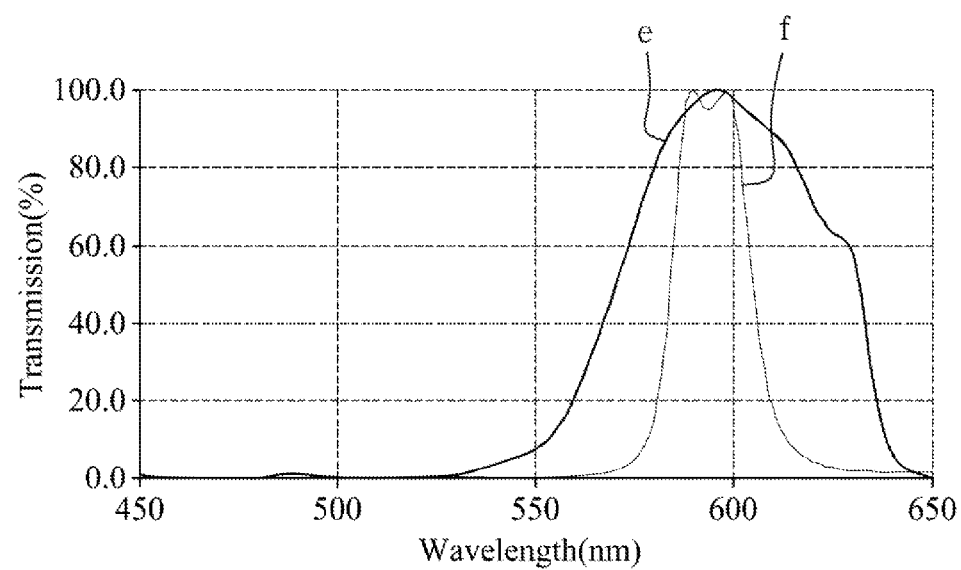
FIG. 12 is a combined-spectrum of a combination of the second light emitting diode panel and the second narrow band filter.

FIG. 12 is a combined-spectrum of a combination of the second light emitting diode panel 102 and the second narrow band filter 106. The second light emitting diode panel 102 utilizes organic light emitting diode panel as lighting source, and only wavelength band that is matched with the wavelength ranges of the spectrum of the second narrow band filter 106 can be passed through. Therefore, the peak wavelength at 595 nm of the second light emitting diode panel 102 can be concentrated, and unnecessary wavelength band can be filtered for reducing the bad influence on the therapy of cosmetic effect.

Figure 13:
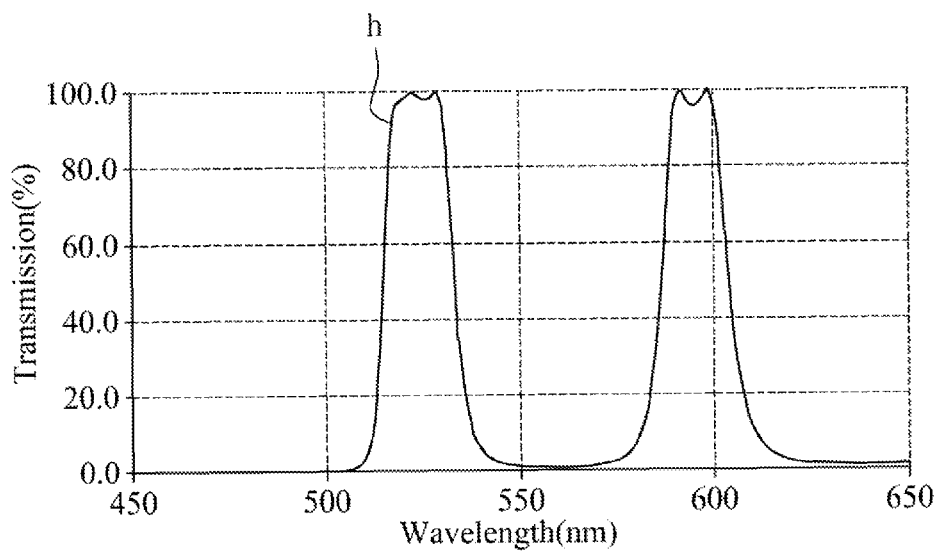
FIG. 13 is a transmission spectrum of the narrow band filter in FIG. 2.

FIG. 13 is a transmission spectrum h of the narrow band filter 107 in FIG. 2. In FIG. 2, the narrow band filter 107 is a multiple frequency-range narrow band filter, and can replace the usage of the first narrow band filter 105 and the second narrow band filter 106 with only one multiple frequency-range narrow band filter 107. In FIG. 13, the transmission spectrum h has two-peak wavelength, 525 nm and 595 nm. Therefore, it is possible to produce two wavelength bands by only one multiple frequency-range narrow band filter 107. The narrow band filter 107 is made by vacuum coating method, and is made of a stacked structure on a substrate, in which the stacked structure includes 37 layers of an overlapping of high/low refractive index layers. The thickness of the stacked structure is 2.62 μm.

Figure 14:
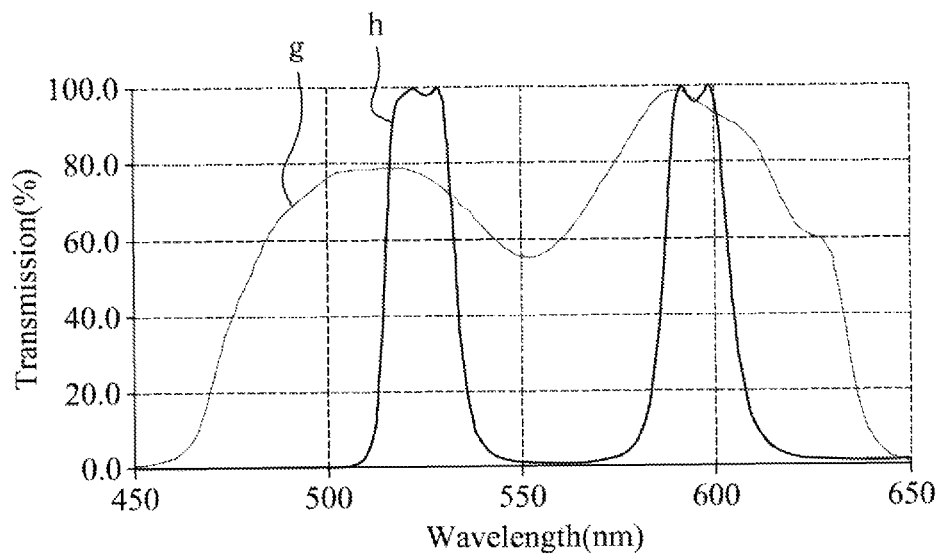
FIG. 14 is a combined-spectrum of the first light emitting diode panel, the second light emitting diode panel, and the narrow band filter.

FIG. 14 is a combined-spectrum of the first light emitting diode panel 101, the second light emitting diode panel 102, and the narrow band filer 107. In FIG. 14, the composite spectrum of the first light emitting diode panel 101 and the second light emitting diode panel 102 is g. The narrow band filter 107 is disposed on a surface 103a of the optical window 103, and only the wavelength band that is matched with the wavelength ranges of the transmission spectrum h of the narrow band filter 107 can be passed through. Therefore, one multiple frequency-range narrow band filter 107 can be used to replace two single frequency-range narrow band filters 105, 106, so that the manufacturing cost can be reduced.

Figure 15:
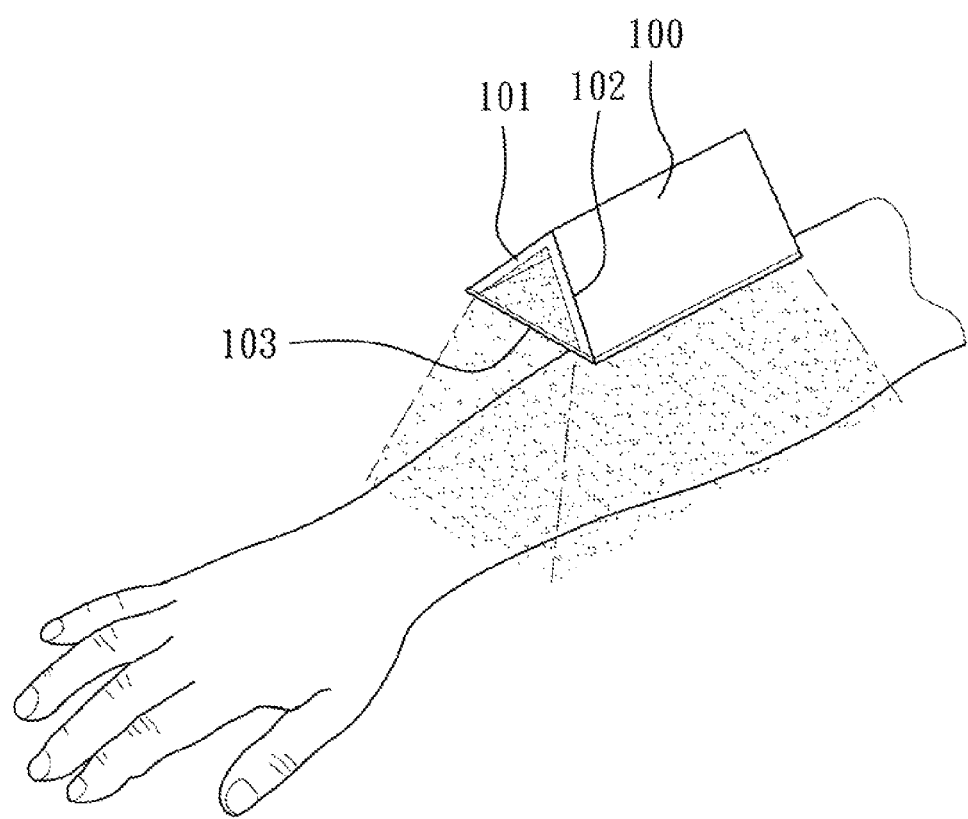
FIG. 15 is a schematic view showing the usage status of the light emitting diode-based skin cosmetic device.

FIG. 15 is a schematic view showing the usage status of the light emitting diode-based skin cosmetic device 100. The emitting lights of the first light emitting diode panel 101 and the second light emitting diode panel 102 pass through the optical window 103 and irradiate to human's skin. The first light emitting diode panel 101 and the second light emitting diode panel 102 utilize organic light emitting diode panels as lighting source. The first light emitting diode panel 101 and the second light emitting diode panel 102 can emit lights individually or simultaneously, and the emitted lights thereof can have a selected single wavelength band or two different wavelength bands simultaneously by controlling the power of the two panels.

To sum up, a light emitting diode-based skin cosmetic device is disclosed. The light emitting diode-based skin cosmetic device of the disclosure utilizes a combination of an organic light emitting diode panel and a narrow band filter. Therefore, a uniform to light intensity and a precision control of the peak wavelength are obtained. The wavelength can be concentrated through the narrow band filter, and unnecessary wavelength band is filtered for achieving better therapy or cosmetic effect. In addition, the improvement structures of the light emitting diode-based skin cosmetic device make it possible to achieve multiple-wavelength band cosmetic effect without extending the volume thereof, and make it suitable for home use due to the compact size thereof. Moreover, utilizing the organic light emitting diode panel as light source can have many advantages, such as smooth light color, proper light energy, high security, low energy consumption, thin in thickness and portability, as compared to its inorganic light emitting diode counterpart. The two individual narrow band filters may also be combined together as a multiple wavelength-range narrow band filter and deposited on the light emerging surface of the optical window instead in case of demands.

It will be apparent to those skilled in the art that various modifications and variations can be made to the structure of the present disclosure without departing from the scope or spirit of the disclosure. In view of the foregoing, it is intended that the present disclosure covers modifications and variations of this disclosure provided they fall within the scope of the following claims.

What is claimed is:

1. A light emitting diode-based skin cosmetic device, comprising:
   a plurality of double-faced light emitting panels, each of the double-faced light emitting panel comprises at least one light emitting, diode source, wherein the plurality of double-faced light emitting panels are mutually connected at one side, and an angle is formed between each two adjacent double-faced light emitting panels, and the light emitting diode source is an organic light emitting diode, the light emitting diode source is an organic light emitting, diode panel with double-faced lighting or an organic light emitting diode panel with single-faced lighting; and
   a plurality of optical Windows, wherein two sides of each optical window are connected with open sides of each two adjacent double-faced light emitting panels to form a closed triangle structure, and the angle between each two adjacent double-faced light emitting panels is faced toward each optical window;
   wherein wavelength bands emitted from one face of each two adjacent double-faced light emitting panels are overlapped on each optical window that connected with each two adjacent double-faced light emitting panels to form a mixed wavelength band.

2. The light emitting diode-based skin cosmetic device of claim 1, wherein the plurality of double-faced light emitting panels are mutually connected to form a serration-liked appearance.

3. The light emitting diode-based skin cosmetic device of claim 1, wherein the light emitting diode source comprises a fluorescence material, a phosphorescence material, or a mixture of the two thereof.

4. The light emitting diode-based skin cosmetic device of claim 1, wherein each double-faced light emitting panel comprises one organic light emitting diode panel with double-faced lighting.

5. The light emitting diode-based skin cosmetic device of claim 1, wherein each double-faced light-emitting panel comprises two organic light emitting diode panels each with single-faced lighting.

6. The light emitting diode-based skin cosmetic device of claim 1, wherein two lighting surfaces of each double-faced light emitting panel emit the same or different wavelength band.

7. The light emitting diode-based skin cosmetic device of claim 6, when the two lighting surfaces of each double-faced light emitting panel emit the same wavelength band, it indicates that the wavelength band of the light emitting diode source is selected from one of 450±10 nm, 595±10 nm, 525±10 nm or 640±10 nm.

8. The light emitting diode-based skin cosmetic device of claim 6, when the two lighting surfaces of each double-faced light emitting panel emit different wavelength band, it indicates that the wavelength band of the light emitting diode source is an assembly that is selected from any two of 450±10 nm, 595±10 nm, 525±10 nm or 640±10 nm.

9. The light emitting diode-based skin cosmetic device of claim 6, further comprising:
  at least one narrow band filter, the narrow band filter is disposed on each surface of the double-faced light-emitting panel or on the optical window.

10. The light emitting diode-based skin cosmetic device of claim 9, wherein the narrow band filter is a single frequency-range or a multiple frequency-range narrow band filter.

11. The light emitting diode-based skin cosmetic device of claim 9, wherein the narrow band filter comprises multiple optical interference layers.

\* \* \* \* \*